(12) United States Patent
Adrian et al.

(10) Patent No.: US 6,452,006 B1
(45) Date of Patent: Sep. 17, 2002

(54) METHOD FOR PREPARING 5-(1-METHYLETHYL)-6-(PHENYLMETHYL) PYRIMIDINE-2,4(1H,3H)-DIONE

(75) Inventors: Guy Adrian, Brignais; François Lecoutteux; Sylviane Mignonac, both of Lyons, all of (FR)

(73) Assignee: Sylachim, Chasse sur Rhone (FR)

( * ) Notice: Subject to any disclaimer, the term of this patent is extended or adjusted under 35 U.S.C. 154(b) by 0 days.

(21) Appl. No.: 09/743,463

(22) PCT Filed: Jul. 15, 1999

(86) PCT No.: PCT/FR99/01723
§ 371 (c)(1),
(2), (4) Date: May 7, 2001

(87) PCT Pub. No.: WO00/03999
PCT Pub. Date: Jan. 27, 2000

(30) Foreign Application Priority Data

Jul. 16, 1998 (FR) .............................. 98 09085

(51) Int. Cl.$^7$ ............................................. C07D 239/54
(52) U.S. Cl. ..................................................... 544/309
(58) Field of Search ......................................... 544/309

(56) References Cited

U.S. PATENT DOCUMENTS 5,474,996 A 12/1995 Uclaf .......................... 514/256

FOREIGN PATENT DOCUMENTS

| EP | 420 763 | 4/1991 |
| EP | 515 265 | 11/1992 |

Primary Examiner—John M. Ford
(74) Attorney, Agent, or Firm—Dennison, Schultz & Dougherty

(57) ABSTRACT

The invention relates to a process for the preparation of 5-(1-methylethyl)-6-(phenylmethyl)pyrimidine-2,4(1H,3H)-dione.

5 Claims, No Drawings

METHOD FOR PREPARING 5-(1-METHYLETHYL)-6-(PHENYLMETHYL) PYRIMIDINE-2,4(1H,3H)-DIONE

BACKGROUND OF THE INVENTION

A subject-matter of the present invention is a process for the preparation of 5-(1-methylethyl)-6-(phenylmethyl) pyrimidine-2,4(1H,3H)-dione of formula (I):

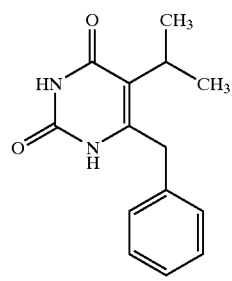

(I)

The compound of formula (I) is known in itself. It can, in particular, be used as intermediate in the synthesis of active compounds which are inhibitors of HIV (Human Immunodeficiency Virus) reverse transcriptase of general formula:

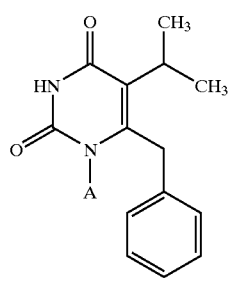

(II)

in which

A represents an RaOCH(Rb)— group, where Ra is a ($C_{1-6}$)alkyl group and Rb is a ($C_{1-4}$)alkyl group or a hydrogen atom.

Various processes for the synthesis of the compounds of formula (II) are disclosed in Patents EP 631 783 and JP 080003143 or in Tanaka H. et al., *J. Med. Chem.* (1995), 38(15), 2860–2865. The starting material used is 5-(1-methylethyl)pyrimidine-2,4(1H, 3H)-dione, an expensive product which has to be prepared in several stages, including a stage of hydrogenation in a highly dilute acidic medium. 5-(1-Methylethyl)pyrimidine-2,4(1H,3H)-dione then leads to the compound of formula (II) in four synthetic stages: alkylation with chloromethyl ethyl ether, condensation of the lithium salt of the first stage with benzaldehyde at a very low temperature and reduction by hydrogenolysis of the benzyl alcohol derivative thus obtained after acetylation of the alcohol functional group by the action of acetic anhydride. The yields are greater than 70–80%, except during the lithiation stage, which involves operating in a dilute medium, at low temperature, using organometallic reagents, such as butyllithium or hexyllithium.

In Danel K. et al., *J. Med. Chem.* (1996), 39(12), 2427–2431, another way of carrying out the preparation is described which circumvents the obstacle of the lithiation and uses readily accessible starting materials, such as phenylacetonitrile, to which is added ethyl 2-bromo-2-isopropylacetate via a Reformatsky reaction. The intermediate ethyl 2-isopropyl-4-phenylacetoacetate thus prepared is cyclized to 5-(1-methylethyl)-6-(phenylmethyl)-2-thioxo-2,3-dihydropyrimidine-4(1H)-one by the action of thiourea and then, finally, the compound of formula (I) is obtained by the action of chloroacetic acid. This synthesis is ponderous and involves carrying out a Reformatsky reaction on an industrial scale and thus the use of very large amounts of zinc, which is difficult to employ. Furthermore, the desulphurization of 5-(1-methylethyl)-6-(phenylmethyl)-2-thioxo-2,3-dihydropyrimidine-4(1H)-one with chloroacetic acid is accompanied by the formation of chlorothioacetic acid, a product with a nauseating smell. These processes thus comprise numerous stages and use either expensive starting materials or difficult reaction conditions which involve specific safety conditions.

SUMMARY OF THE INVENTION

The Applicant Company has consequently looked for a novel process which obviates the abovementioned disadvantages, making possible simpler, more economical and safer processing.

A first subject-matter of the present invention is consequently a novel process for the preparation of the compounds of formula (I) as defined above and all the alternative forms thereof. Another subject-matter of the invention is novel compounds of use in particular as synthetic intermediates.

DETAILED DESCRIPTION OF THE INVENTION

The process according to the invention is illustrated by the following scheme:

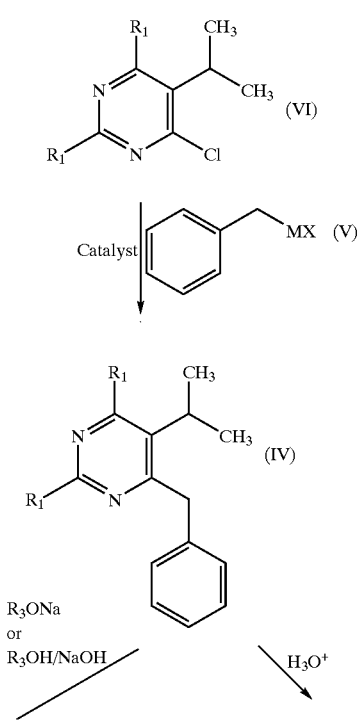

Scheme 1

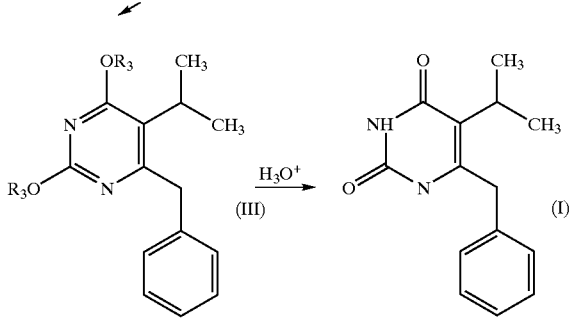

In the context of the present application,
M represents an alkali metal or any other metal of Class II and III of the Periodic Classification of the Elements. More particularly, M represents a manganese, tin, zinc, iron, magnesium or copper atom. X represents a halogen atom, such as chlorine, bromine or iodine,
$R_1$ represents a halogen atom or an —$OR_2$ group, where $R_2$ represents a ($C_{1-4}$)alkyl group,
$R_3$ represents a ($C_{1-4}$)alkyl group.

The process according to the invention consists in reacting a compound of formula (VI), in which $R_1$ is as defined above, by coupling with an organometallic compound of formula (V), in which M and X are as defined above, in the presence of a homogeneous metal catalyst, in order to obtain the compound of formula (IV) in which $R_1$ is as defined above. This coupling process and all the alternative forms thereof come within the scope of the present invention.

At this point, this compound of formula (IV) can either be directly hydrolysed with a strong acid, in an aqueous medium, in an alcoholic solvent such as ethanol or isopropanol, or, when $R_1$ represents a halogen atom, a dialkoxylation can be carried out by conventional methods known to a person skilled in the art, before carrying out the hydrolysis of this compound obtained of formula (III) under the same hydrolysis conditions as above. This dialkoxylation can be carried out, for example, by the action of alkoxides of formula $R_3$ONa according to methods known to a person skilled in the art or by the action of alcohols of formula $R_3$OH in the presence of a strong base in aqueous solution, such as dilute sodium hydroxide.

The organometallic compound of formula (V) can be chosen, for example, from: a benzylmagnesium halide or a benzylzinc halide. The benzylmagnesium halide is preferred and more particularly benzylmagnesium chloride is preferred.

According to another specific embodiment of the coupling of the compound of formula (VI) with a compound of formula (V), this coupling can be carried out under the conditions of the Barbier reaction (Barbier P., CR, 1899, 128–110), that is to say the addition of a benzyl halide to the compound of formula (VI) in the presence of magnesium turnings, in an appropriate solvent. In the context of the present invention, benzyl chloride is preferred as benzyl halide. This appropriate solvent can be an ether, such as ethyl ether or tetrahydrofuran, or an acetal, such as methylal or ethylal.

According to an advantageous process of the invention, the catalyst is a derivative either of nickel or of palladium. It can be chosen from homogeneous metal catalysts derived either from nickel or from palladium which are complexed with ligands, such as acetylacetone, triarylphosphines or 1,n-bis(diarylphosphino)alkanes, of expanded formula Ni(Acac)$_2$, NiCl$_2$[PR$_3$]$_2$, NiBr$_2$[PR$_3$]$_2$, NiCl$_2$[R$_2$P(CH$_2$)$_n$PR$_2$], Pd[P(R)$_3$]$_4$, PdCl$_2$[PR$_3$]$_2$, and the like, where Acac is the acetylacetonate group and R is a (C$_{1-6}$)alkyl, aryl or heteroaryl group. The term "aryl group" is understood to mean a carbonaceous aromatic nucleus, for example phenyl, naphthyl or anthracenyl, and the term "heteroaryl group" is understood to mean an aromatic heterocycle, such as, for example, pyridine or thiophene. The preferred catalysts have the following expanded formulae: [CH$_3$COCH═C(O—)CH$_3$]$_2$Ni, NiCl$_2$[(C$_6$H$_5$)$_2$PCH$_2$—CH$_2$P(C$_6$H$_5$)$_2$] or NiCl$_2$[(C$_6$H$_5$)$_3$P]$_2$.

The reaction according to the invention can be carried out in a polar aprotic solvent (such as tetrahydrofuran, isopropyl ether or diethoxymethane) or in a mixture of polar solvents as defined above and nonpolar solvents, such as aromatic hydrocarbons (toluene, heptane, and the like).

The coupling stage, according to either one of the two alternative forms described above, can be carried out at a temperature of between −80 and +110° C. Generally, the molar ratio of the compound of formula (VI) to the organometallic compound of formula (V) is between 0.5 and 1.5, preferably between 0.9 and 1.2. When the coupling is carried out under the Barbier conditions as described above, the molar ratio of the compound of formula (VI) to the benzyl halide is between 1 and 3, preferably between 1.1 and 1.5, and he molar ratio of the magnesium to the benzyl halide is between 1 and 5, preferably between 1 and 2. The molar ratio of the compound of formula (VI) to the catalyst can be between lo and 30% by weight with respect to the compound of formula (VI). The strong acid used during the hydrolysis can be chosen from hydrochloric acid, hydrobromic acid, sulphuric acid or alkanesulphonic acid, such as methanesulphonic acid. To a lesser extent, acetic acid can also be used.

The compounds of formula (IV) and (III) are novel and come within the scope of the invention.

The compounds of the invention of formula (VI) where $R_1$ is a chlorine atom, which will be named compounds of formula (VIa), can be prepared according to the following Scheme 2, which uses a procedure known in the literature.

Scheme 2

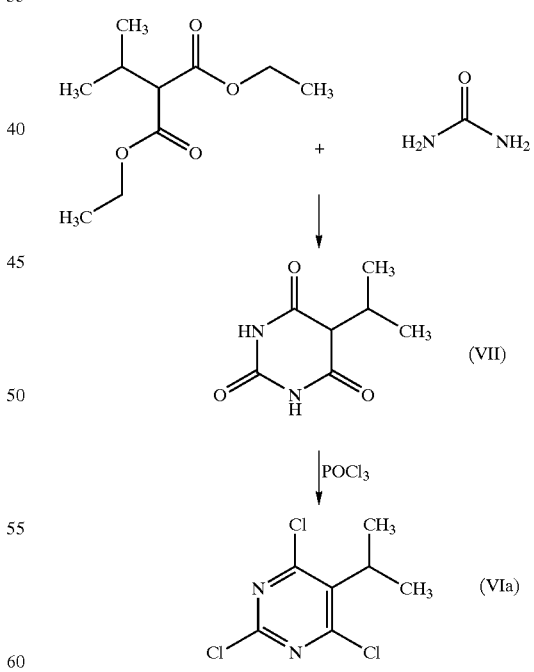

According to Scheme 2, urea is reacted with diethyl isopropylmalonate (which can be prepared according to conventional methods known to a person skilled in the art or which is alternatively commercially available), in a solvent of alcohol type, at a temperature which can be between 20° C. and the reflux temperature of the solvent, in order to obtain 5-(1-methylethyl)pyrimidine-2,4,6(1H,3H,5H)-trione of formula (VII). This compound of formula (VII) is subsequently reacted with phosphorus oxychloride under the conditions described in J. Baddiley et al., *J. Chem. Soc.*, 678(1944), I. Wempen et al., *J. Med. Chem.*, 6(1963), 688–693 or Gershon et al., *J. Med. Chem.*, 7(1964), 808–809, at a temperature of 20 to 160° C., in order to obtain 2,4,6-trichloro-5-(1-methylethyl)-pyrimidine of formula (VIa). Following the reaction of the compound (VII) with phosphorus oxychloride, use may particularly be made either of an agent for trapping the acidity, such as a dialkylaniline, or of an amine hydrochloride.

Other procedures known in the literature, for example in H. Koroniak et al., *Org. Prep. Proced. Int.*, 25 (1993), 5 563–568, can also be used in order to obtain 5-(1-methylethyl)pyrimidine-2,4,6(1H,3H,5H)-trione of formula (VII). It is also commercially available.

According to the process of the present invention, the crude products can be used in the successive synthetic stages from the stage involving the compound of formula (VII) to the production of the compound of formula (I).

The compounds of formula (VI), in which $R_1$ is an —$OR_2$ group where $R_2$ represents a $(C_{1-4})$alkyl group, can be obtained from 2,4,6-trichloro-5-(1-methylethyl)-pyrimidine of formula (VIa) by dialkoxylation of 2,4,6-trichloro-5-(1-methylethyl)pyrimidine, which can be carried out under the conditions of the dialkoxylation described above.

In order to obtain the compounds of formula (II) in which A represents an RaOCH(Rb)— group, where Ra is a $(C_{1-6})$ alkyl group and Rb is a $(C_{1-4})$alkyl group or a hydrogen atom, use is made of the method disclosed in Danel K. et al., *J. Med. Chem.* (1996), 39(12), 2427–2431. This alkylation can also be carried out starting from a compound of formula (I) which is silylated by addition of trimethylsilyl chloride and which is then reacted with an alkoxyalkyl halide. The latter alkylation reaction can be carried out in an aprotic solvent, that is to say either in a halogenated solvent, such as dichloromethane, chloroform or chlorobutane, or in a polar solvent, such as tetrahydrofuran, diethoxymethane, dioxane, and the like. This reaction of alkylation by an alkoxyalkyl halide can also be carried out according to the procedure disclosed in Patent Application Wo 95/18109, whereas, in this patent application, R is an allyl and propargyl group. This reaction is carried out in polar solvents, such as dimethylformamide or dimethyl sulphoxide, in the presence of a base, such as potassium carbonate.

A third subject-matter of the invention is thus a process for the preparation of the compounds of formula (II) from the compound of formula (I) prepared according to the novel process described above.

The following examples illustrate the reparation process according to the invention. The NMR analyses confirm the structures of the compounds obtained.

EXAMPLE 1

Preparation of 5-(1-methylethyl)pyrimidine-2,4,6 (1H,3H,5H)-trione 456 g (2.25 mol) of diethyl isopropylmalonate, 650 ml of a 30% methanolic sodium methoxide solution and 910 ml of methanol are charged to a 2 liter reactor equipped with an anchor stirrer. The mixture is brought to reflux for thirty minutes before adding 135 g (2.25 mol) of urea in the solid form while maintaining the reflux. The reaction mixture at the end of the reaction is a thick white suspension which is brought to dryness by evaporation of the methanol under vacuum. The residue is taken up in 1370 ml of water and then filtered after cooling to 20° C. The filtrate is treated by addition of the amount of hydrochloric acid needed to bring the pH to 2–3, and the precipitate obtained is filtered off under cold conditions and washed with ice-cold water in order to obtain 267 g of 5-(1-methylethyl)pyrimidine-2,4,6 (1H,3H,5H)-trione.

(Yield=69%)

Melting point: 215° C.

EXAMPLE 2

Preparation of 2,4,6-trichloro-5-(1-methylethyl) pyrimidine 267 g (1.57 mol) of 5-(1-methylethyl)-pyrimidine-2,4,6 (1H,3H,5H)-trione and 526 ml of phosphorus oxychloride are placed in a 2 liter reactor equipped with an anchor stirrer. The mixture is brought to 90° C. and 250 ml of diethylaniline are rapidly added while allowing the exotherm to take place up to 110° C. After maintaining at 105° C. for 5 hours, the medium is cooled to 20° C. and diluted by addition of 534 ml of isopropyl ether. The fluid medium obtained is run onto a stirred two-phase mixture of water (800 ml) and of isopropyl ether (1070 ml), the rise in temperature being controlled so as not to exceed 35° C. The upper two-phase organic phase is separated and washed with 270 ml of water, sodium hydroxide solution being added until a pH of the aqueous phase of 7 is obtained. After an additional washing with water, the organic phase is concentrated under vacuum and the residue taken up in 530 ml of isopropyl alcohol and water. The mixture is brought to 50° C. in order to dissolve, 400 ml of water are added and the mixture is cooled to 0° C. The white precipitate formed is filtered off and washed with a mixture of water and of isopropyl alcohol in order to obtain 309 g of 2,4,6-trichloro-5-(1-methylethyl)-pyrimidine.

(Yield=87%)

Melting point: 69.4° C.

EXAMPLE 3

Preparation of 2,4-dichloro-5-(1-methylethyl)-6-(phenylmethyl)pyrimidine

The fine suspension obtained by mixing 30 g (0.133 mol) of the compound of Example 2, 300 ml of tetrahydrofuran and 2.1 g of nickel(II) .1,2-bis-(diphenylphosphino)ethane chloride (NiCl$_2$.dppe) is brought to 0° C. in a 0.5 liter reactor, rendered inert with nitrogen and equipped with an anchor stirrer, and treated by the addition of 66.5 ml (0.133 mol) of a 2M solution of benzylmagnesium chloride in tetrahydrofuran without exceeding 10° C.

At the end of the progression of the coupling, the reaction mixture is treated by the addition of 60 ml of a 9% ammonium chloride solution, the upper organic phase is separated, washed with an additional 60 ml of a 9% ammonium chloride solution and evaporated to dryness, and the residue is taken up in isopropyl ether and washed successively with a dilute 10% citric acid solution and then with water. After distillation of the solvent, the product is purified by distillation under vacuum in order to result in 20 g of 2,4-dichloro-5-(1-methylethyl)-6-(phenylmethyl) pyrimidine (yellow oil).

(Yield=57%)

The product obtained can be crystallized from ethanol as in Example 4.

Melting point: 61–63° C.

EXAMPLE 4

Preparation of 2,4-dichloro-5-(1-methylethyl)-6-(phenylmethyl)pyrimidine

The fine suspension obtained by mixing 40 g (0.177 mol) of the compound of Example 2, 200 ml of toluene and 2 g of nickel catalyst NiCl$_2$.dppe is brought to 0° C. in a 0.5 liter reactor, rendered inert with nitrogen and equipped with an anchor stirrer, and treated by addition of 97.6 ml (0.195 mol) of a 2M solution of benzylmagnesium chloride in tetrahydrofuran without exceeding 10° C. At the end of the progression of the coupling, the reaction mixture is treated by addition of 120 ml of a 10% ammonium chloride solution and the upper organic phase is separated, washed with 10% aqueous ammonium chloride solution until decoloured and evaporated to dryness under vacuum. The oily residue obtained is purified by distillation under vacuum in order to remove, as distillation tops, the residual starting material and to result in 39.6 g of 2,4-dichloro-5-(1-methylethyl)-6-(phenylmethyl)pyrimidine (yellow oil, boiling temperature at 0.2 mbar=145–150° C.).

(Yield=79%)

This product recrystallizes from ethanol.

Melting point: 61–63° C.

EXAMPLE 5

Preparation of 5-(1-methylethyl)-6-(phenylethyl)pyrimidine-2,4(1H,3H)-dione

The compound of Example 3 or Example 4 (15 g; 0.053 mol) is brought to reflux for several hours in a mixture of 75 ml of hydrochloric acid and 135 ml of ethanol. At the end of the reaction, the ethanol is distilled off at atmospheric pressure and 75 ml of water are added. The precipitate obtained is filtered off at 5° C. and washed with water and then with 45 ml of ethyl acetate in order to result, after drying, in 8.5 g of 5-(1-methylethyl)-6-(phenylmethyl)pyrimidine-2,4(1H,3H)-dione.

(Yield=65%)

Melting point: 244–246° C.

EXAMPLE 6

Preparation of 5-(1-methylethyl)-2,4-dimethoxy-6-(phenylmethyl)pyrimidine 67.6 g of 30% sodium methoxide in methanol are added to the solution of 2,4-dichloro-5-(1-methylethyl)-6-(phenylmethyl)pyrimidine in isopropyl ether obtained from 28.2 g (0.125 mol) of 5-isopropyl-2,4,6-trichloropyrimidine. When there is no more change, 75 ml of water are added and the organic and aqueous phases are separated. The organic phase is washed with water and is dried by evaporation of the solvent under vacuum (to 6 mbar) in order to obtain 32 g of crude 5-(1-methylethyl)-2,4-dimethoxy-6-(phenylmethyl)-pyrimidine.

This product can be purified by distillation (cf. Example 9).

Boiling point: 294–298° C.

EXAMPLE 7

Preparation of 5-(1-methylethyl)-6-(phenylmethyl)pyrimidine-2,4(1H,3H)-dione

The crude compound of Example 6 (27 g, 0.09 mol) is brought to reflux for several hours in a mixture of 90 ml of hydrochloric acid and 135 ml of ethanol. At the end of the reaction, the ethanol is distilled off under atmospheric pressure and 100 ml of water are added. The precipitate obtained is filtered off at 5° C. and then washed successively with water and with 45 ml of ethyl acetate in order to result, after drying, in 14.5 g of 5-(1-methylethyl)-6-(phenylmethyl)pyrimidine-2,4(1H,3H)-dione.

(Yield=56% with respect to the 2,4,6-trichloro-5-(1-methylethyl)pyrimidine)

Melting point: 240–242° C.

EXAMPLE 8

Preparation of 6-chloro-2,4-dimethoxy-5-(1-methylethyl)pyrimidine 112 g of 30% sodium methoxide in methanol are added, in a 0.5 liter reactor rendered inert with nitrogen and equipped with an anchor stirrer, to the solution of compound of Example 2 (70 g, 0.31 mol) in 400 ml of isopropyl ether. The medium is kept stirred at ambient temperature. When there is no more change, 140 ml of water are added and the organic and aqueous phases are separated. The organic phase is washed with water and dried by evaporation of the solvent under vacuum. The oily residue is distilled under vacuum in order to obtain 53 g of purified 6-chloro-2,4-dimethoxy-5-(1-methylethyl)pyrimidine (oil, boiling temperature at 13 mbar=128–30° C.), which comprises approximately 5% of positional isomer.

(Yield=79%)

EXAMPLE 9

Preparation of 2,4-dimethoxy-5-(1-methylethyl)-6-(phenylmethyl)pyrimidine 0.15 g of nickel catalyst of expanded formula Ni(Acac)$_2$ is added, in a 0.25 liter three-necked Erlenmeyer flask rendered inert with nitrogen, at a temperature below 5° C. and in one step, to the mixture in solution of 15 g (0.07 mol) of the compound of Example 8, 150 ml of tetrahydrofuran and 34.6 ml (0.07 mol) of a 2M solution of benzylmagnesium chloride in tetrahydrofuran. The medium is brought back to ambient temperature and, at the end of the progression of the coupling, treated by addition of 50 ml of a 10% ammonium chloride solution. The upper organic phase is separated, washed with an additional 50 ml of a 10% ammonium chloride solution and then washed with water. The organic phase is evaporated to dryness in order to obtain an oily residue (boiling temperature under 5 mbar= 140–150° C.) which is purified again by chromatography on silica gel, elution being carried out with toluene, in order to result in 3.2 g of 2,4-dimethoxy-5-(1-methylethyl)-6-(phenylmethyl)pyrimidine.

Boiling point: 294–298° C.

EXAMPLE 10

Preparation of 1-(ethoxymethyl)-5-(1-methylethyl)-6-(phenylmethyl)pyrimidine-2,4(1H,3H)-dione 5 g of the compound of the preceding Example 5 or Example 7, in solution of 30 ml of methylene chloride, are silylated by addition of 5.7 ml of trimethylsilyl chloride, followed by 6.6 ml of triethylamine. 2 g of chloromethyl ethyl ether, in solution in methylene chloride, are added at ambient temperature and the medium is stirred until the end of the reaction. The mixture is treated by addition of 30 ml of water and the organic phase is separated, washed with 30 ml of water and evaporated to dryness. The oily residue is crystallized from a mixture of isopropanol and of water in order to obtain 5.2 g of dry 1-(ethoxymethyl)-5-(1-methylethyl)-6-(phenylmethyl)pyrimidine-2,4(1H,3H)-dione.

(Yield=84%)

Melting point: 110.9° C.

EXAMPLE 11

Preparation of 2,4,6-trichloro-5-(1-methylethyl) pyrimidine 60 g (0.353 mol) of 5-(1-methylethyl)-pyrimidine-2,4,6-(1H,3H,5H)-trione and 194.6 g (1.27 mol) of phosphorus oxychloride are placed in a 0.5 liter reactor equipped with an ink stirrer. The mixture is brought to 80° C. and 104.5 g (0.7 mol) of diethylaniline are rapidly added while allowing the exotherm to take place. After maintaining at 105° C. for 6 hours, the medium is cooled to 50° C. and diluted by addition of 240 ml of toluene. This fluid medium, brought back to 20° C., is run onto 240 ml of water while avoiding a temperature of 65° C. from being exceeded. The separated upper organic phase is washed successively with water, with dilute sodium hydroxide solution and then with water until a pH of the aqueous phase of 7 is achieved.

The organic phase, dried by azeotropic distillation, is used directly in the subsequent stage.

(Yield, calculated after HPLC assay with external calibration=92.6%)

EXAMPLE 12

Preparation of 2,4-dichloro-5-(1-methylethyl)-6-(phenylmethyl)pyrimidine

The toluene solution from the preceding example is placed, with 0.55 g of NiCl$_2$-dppe, in a 0.5 liter reactor rendered inert with nitrogen and equipped with an ink stirrer. The suspension obtained is brought to 0° C. and 268.3 g (0.356 mol) of 20% w/w benzylmagnesium chloride in tetrahydrofuran are added thereto without exceeding 5° C.

At the end of the reaction, the reaction mixture is treated by running in 110 ml of a 10% ammonium chloride solution and then the organic phase is washed successively with 10% ammonium chloride solutions and then with water until a neutral pH is achieved. After removing the solvents by distillation, the product is isolated by crystallization from 95 ethanol.

(Yield of the two stages=60.8%)

Melting point: 61.6° C.

EXAMPLE 13

Preparation of 2,4-dichloro-5-(1-methylethyl)-6-(phenylmethyl)pyrimidine 175.8 g of a toluene solution of compound obtained according to Example 11 from 55 g (0.323 mol) of 5-(1-methylethyl)pyrimidine-2,4,6-(1H,3H,5H)-trione are placed in a 0.5 liter reactor, rendered inert with nitrogen and equipped with an anchor stirrer, with 0.55 g of catalyst NiCl$_2$[P(C$_6$H$_5$)$_3$]$_2$ and the solution is treated by addition of 292.6 g (0.388 mol) of 20% w/w benzylmagnesium chloride in tetrahydrofuran without exceeding 5° C.

At the end of the progression of the coupling, the medium is hydrolysed with 110 ml of 1.6% aqueous hydrochloric acid, washing is carried out with water, the organic phase is evaporated to dryness under vacuum and the residue is used as is in the following stage.

EXAMPLE 14

Preparation of 5-(1-methylethyl)-6-(phenylmethyl) pyrimidine-2,4-(1H,3H)-dione 50 g of compound of Example 12 are brought to reflux for 16 hours in a mixture of 200 ml of ethanol, 50 ml of water and 50 ml of sulphuric acid. At the end of the reaction, the ethanol is distilled off under atmospheric pressure, 100 ml of water are added and then the pH of the medium is brought to 2/3 by running in 30% sodium hydroxide solution. The precipitate obtained is filtered off, washed with water and washed with acetone in order to lead, after drying, to 30.6 g of 5-(1-methylethyl)-6-(phenylmethyl)pyrimidine-2,4-(1H, 3H)-dione.

(Yield=70.5%)

Melting point: 245.2° C.

EXAMPLE 15

Preparation of 2,4-dichloro-5-(1-methylethyl)-6-(phenylmethyl)pyrimidine According to the Barbier Method 1 g (4.4 mmol) of 2,4,6-trichloro-5-(1-methylethyl) pyrimidine, in solution in diethyl ether, is placed with 0.21 g of magnesium and 0.001 g of NiCl$_2$[P(C$_6$H$_5$)$_3$]$_2$ in a mechanically stirred 50 ml three-necked flask rendered inert with nitrogen. The suspension obtained is brought to 20° C. and 0.66 g (5.2 mmol) of magnesium chloride is added thereto and the initiation of the magnesium compound is observed. At the end of the reaction, the reaction mixture is treated with a 10% ammonium chloride solution and then the organic phase is washed successively with 10% ammonium chloride solutions and then with water until a neutral pH is achieved.

After removing the solvents by distillation, 400 mg of product are isolated by chromatography on silica, elution being carried out successively with heptane and then with a heptane/ethyl acetate mixture.

What is claimed is:
1. A process for the preparation of 5-(1-methyethyl)-6-(phenylmethyl)pyrimidine-2,4-(1H,3H)-dione of formula (I):

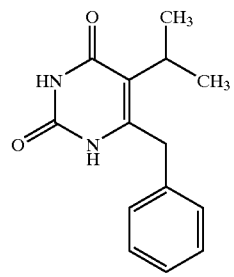

(I)

comprising the steps of reacting a compound of formula (VI):

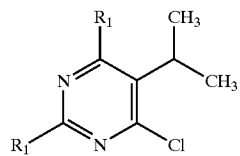

(VI)

by coupling, in the presence of a homogeneous metal catalyst, either with an organometallic compound of formula (V):

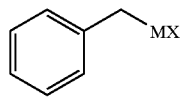

(V)

in which M represents an alkali metal or other metal of Group II or Group III of the periodic table, and X represents a halogen atom, or with a benzyl halide in the presence of magnesium, to obtain a compound of formula (IV):

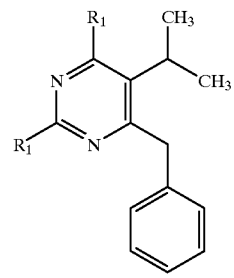

(IV)

and, where $R_1$ is $OR_2$ or a halogen atom, subjecting the compound of formula (IV) to acid hydrolysis, or where $R_1$ is a halogen atom, subjecting the compound of formula (IV) to dialkoxylation followed by acid hydrolysis, to obtain the compound of formula (I).

2. A process according to claim 1, wherein the catalyst is a nickel or palladium catalyst completed with a ligand selected from the group consisting of acetylacetone, triarylphosphines and 1,n-bis(diarylphosphino)alkanes, of expanded formula $Ni(Acac)_2$, $NiCl_2(PR_3)_2$, $NiBr_2(PR_3)$, $NiCl_2(R_2P(CH_2)_nPR_2)$, $Pd(P(R)_3)_4$ or $PdCl_2(PR_3)_2$, where Acac is acetylacetonate group and R is a $C_1$–$C_6$ alkyl, aryl or heteroaryl group.

3. A process according to claim 1, wherein the catalyst is selected from the group consisting of $(CH_3COCH=C(O-)CH_3)_2Ni$, $NiCl_2((C_6H_5)_2PCH_2-Ch_2P(C_6H_5)_2)$ and $NiCl_2((C_6H_5)_3P)$.

4. A process according to claim 1, wherein a molar ratio of compound of formula (VI) to the catalyst is from 1 to 30% by weight with respect to the compound of formula (VI).

5. A process according to claim 1, wherein M represents an atom of manganese, tin, zinc, iron, magnesium or copper, and X represents an atom of chlorine, bromine or iodine.

* * * * *